(12) United States Patent
Bieberich

(10) Patent No.: US 7,470,280 B2
(45) Date of Patent: Dec. 30, 2008

(54) CLINICAL GARMENT FOR COMFORT WARMING AND PREWARMING

(75) Inventor: Mark T. Bieberich, Minnetonka, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 623 days.

(21) Appl. No.: 11/057,404

(22) Filed: Feb. 11, 2005

(65) Prior Publication Data

US 2006/0184218 A1 Aug. 17, 2006

(51) Int. Cl.
*A61F 7/00* (2006.01)
(52) U.S. Cl. ................................. 607/104; 607/108
(58) Field of Classification Search ............... 607/104, 607/108; 2/81, 102
See application file for complete search history.

(56) References Cited

U.S. PATENT DOCUMENTS

| | | | |
|---|---|---|---|
| 2,573,414 A | 10/1951 | Dunn | 128/144 |
| 2,826,758 A | 3/1958 | Kahn | 2/81 |
| 3,468,299 A | 9/1969 | D'Amato | 126/204 |
| 3,610,323 A | 10/1971 | Troyer | 165/46 |
| 3,855,635 A | 12/1974 | Ramirez | 2/114 |
| 3,911,499 A | 10/1975 | Benevento et al. | 2/114 |
| 3,950,789 A | 4/1976 | Konz et al. | 2/93 |
| 4,055,173 A | 10/1977 | Knab | 128/139 |
| 4,146,933 A | 4/1979 | Jenkins et al. | 2/2 |
| 4,369,528 A | 1/1983 | Vest et al. | 2/69 |
| 4,494,248 A | 1/1985 | Holder | 2/69 |
| 4,524,463 A | 6/1985 | Ogden | 2/105 |
| 4,558,468 A | 12/1985 | Landry et al. | 2/51 |
| 4,578,825 A | 4/1986 | Vote | 2/114 |
| 4,587,671 A | 5/1986 | Rodriguez, Jr. et al. | 2/69 |
| 4,651,727 A | 3/1987 | Howorth | 128/201.23 |
| 4,653,120 A | 3/1987 | Leaf | 2/114 |
| 4,696,066 A | 9/1987 | Ball et al. | |
| 4,787,101 A | 11/1988 | Feinberg | 2/105 |
| 4,914,752 A | 4/1990 | Hinson et al. | 2/2 |
| 4,964,282 A | 10/1990 | Wagner | 62/259.3 |
| 5,062,424 A | 11/1991 | Hooker | 128/379 |
| 5,255,390 A | 10/1993 | Gross et al. | 2/2 |
| 5,304,213 A | 4/1994 | Berke et al. | 607/104 |
| 5,360,439 A | 11/1994 | Dickerhoff et al. | 607/104 |

(Continued)

FOREIGN PATENT DOCUMENTS

GB 475811 11/1937

(Continued)

OTHER PUBLICATIONS

International Search Report and Written Opinion in PCT/US2005/025355, mailed Dec. 1, 2005.

(Continued)

*Primary Examiner*—Roy D Gibson
(74) *Attorney, Agent, or Firm*—INCAPLAW; Terrance A. Meador

(57) ABSTRACT

A clinical garment having a lower hem and sleeves includes permeable surfaces inside near peripheral portions, a duct in communication with the permeable surfaces, and at least one inlet port opening into the duct. When worn by a patient, the permeable surfaces are positioned adjacent the patient's limbs. Warmed pressurized air may be introduced into the duct and conducted to the permeable surfaces. The warmed pressurized air circulates through the permeable surfaces to warm the adjacent limbs.

17 Claims, 5 Drawing Sheets

U.S. PATENT DOCUMENTS

| | | | |
|---|---|---|---|
| 5,367,710 A | 11/1994 | Karmin | 2/114 |
| 5,411,541 A | 5/1995 | Bell et al. | 607/104 |
| 5,443,488 A | 8/1995 | Namenmye et al. | 607/104 |
| 5,572,742 A | 11/1996 | McFadden | 2/114 |
| 5,575,006 A | 11/1996 | Wolfe | 2/114 |
| 5,611,087 A | 3/1997 | Adkins | 2/114 |
| 5,620,482 A | 4/1997 | Augustine et al. | 607/107 |
| 5,697,963 A | 12/1997 | Augustine | 607/108 |
| 5,785,716 A | 7/1998 | Bayron | 607/108 |
| 5,891,187 A | 4/1999 | Winthrop et al. | 607/96 |
| 5,970,519 A | 10/1999 | Weber | 2/81 |
| 5,974,605 A | 11/1999 | Dickerhoff et al. | 5/421 |
| 6,049,907 A | 4/2000 | Palomo | 2/51 |
| 6,154,883 A | 12/2000 | Spann et al. | 2/69 |
| 6,216,270 B1 | 4/2001 | Moquin et al. | 2/69 |
| 6,235,659 B1 | 5/2001 | McAmish et al. | 442/79 |
| 6,378,136 B2 | 4/2002 | Matsushita | 2/114 |
| 6,484,321 B1 | 11/2002 | Shamam | 2/114 |
| 6,511,501 B1 | 1/2003 | Augustine et al. | 607/96 |
| 6,524,332 B1 | 2/2003 | Augustine et al. | 607/107 |
| 6,524,382 B1 | 2/2003 | Augustine et al. | 607/107 |
| 6,551,347 B1 | 4/2003 | Elkins | |
| 6,571,574 B1 | 6/2003 | Blackstone | 62/420 |
| 6,596,019 B2 | 7/2003 | Turner et al. | 607/108 |
| 6,647,552 B1 | 11/2003 | Hogan | 2/114 |
| 6,694,522 B1 | 2/2004 | Neal | 2/114 |
| 6,792,622 B2 | 9/2004 | Graves | 2/114 |
| 6,799,322 B2 | 10/2004 | Hatton | 2/114 |
| 6,851,125 B2 | 2/2005 | Fujikawa et al. | 2/51 |
| 6,876,884 B2 | 4/2005 | Hansen et al. | 607/98 |
| 7,001,416 B2 | 2/2006 | Augustine et al. | 607/104 |
| 7,226,454 B2 | 6/2007 | Albrecht et al. | 607/104 |
| 7,276,076 B2 | 10/2007 | Bieberich | 607/108 |
| 7,364,584 B2 | 4/2008 | Anderson | |
| 2003/0195596 A1* | 10/2003 | Augustine et al. | 607/104 |
| 2005/0015127 A1 | 1/2005 | Augustine et al. | 607/104 |
| 2005/0143796 A1 | 6/2005 | Augustine et al. | 607/104 |
| 2006/0047332 A1* | 3/2006 | Malmberg et al. | 607/104 |
| 2006/0122671 A1 | 6/2006 | Albrecht et al. | 607/104 |
| 2006/0122672 A1 | 6/2006 | Anderson | 607/104 |
| 2006/0147320 A1 | 7/2006 | Hansen et al. | 417/313 |
| 2006/0184216 A1 | 8/2006 | Van Duren | 607/104 |
| 2006/0184217 A1 | 8/2006 | Van Duren | 607/104 |
| 2006/0184218 A1 | 8/2006 | Bieberich | 607/104 |
| 2006/0259104 A1 | 11/2006 | Panser | 607/104 |
| 2007/0093882 A1 | 4/2007 | Anderson et al. | 607/104 |
| 2007/0093883 A1 | 4/2007 | Anderson et al. | 607/104 |
| 2007/0093884 A1 | 4/2007 | Anderson et al. | 607/104 |
| 2007/0093885 A1 | 4/2007 | Anderson et al. | 607/104 |
| 2007/0239239 A1 | 10/2007 | Albrecht et al. | 607/96 |
| 2008/0027521 A1 | 1/2008 | Bieberich | |
| 2008/0027522 A1 | 1/2008 | Bieberich | |

FOREIGN PATENT DOCUMENTS

| | | |
|---|---|---|
| GB | 1 462 033 | 1/1997 |
| SE | 525 415 | 2/2005 |
| WO | WO 97/14381 A1 | 4/1997 |
| WO | WO 98/48652 | 11/1998 |
| WO | WO 00/62726 | 10/2000 |
| WO | WO 03/086500 A3 | 10/2003 |
| WO | WO 03/106897 A3 | 12/2003 |
| WO | WO 2004/004500 A1 | 1/2004 |
| WO | WO 2006/020170 A1 | 2/2006 |
| WO | WO 2006/062910 A1 | 6/2006 |
| WO | WO 2006/063027 A1 | 6/2006 |
| WO | WO 2006086587 A1 | 8/2006 |
| WO | WO 2007/047917 A1 | 4/2007 |

OTHER PUBLICATIONS

International Search Report and Written Opinion in PCT/US2005/043968, mailed Apr. 19, 2006.

International Search Report and Written Opinion in PCT/US2005/044214, mailed Apr. 19, 2006.

Written Opinion of the International Search Authority (EPO) in PCT/US2006/041028, mailed Feb. 20, 2007.

International Search Report and Written Opinion in PCT/US2006/004644, mailed Dec. 18, 2006.

EPO Examination Report mailed Oct. 24, 2006, in EP03719690.4-1526, EP Regional Phase of PCT/US2003/11128 (published as WO/2003/086500).

Porta-Chill—The Portable Air-Chiller—Brochure, http://www.portachil.com/, Dec. 3, 2002.

P.O. Fanger, Thermal Comfort: Analysis and Applications in Environmental Engineering, Danish Technical Press, 1970, pp. 5-67.

C.B. Mahony & J. Odom, Maintaining intraoperative normothermia: A meta-analysis of outcomes with costs. *AANA Journal*. Apr. 1999. v. 67, No. 2:155-164.

PCT International Publication No. WO 03/086500 A2, Oct. 23, 2003 Arizant Healthcare Inc.

International Search Report and Written Opinion in PCT/US2007/013073, mailed Nov. 9, 2007.

* cited by examiner

CLINICAL GARMENT FOR COMFORT WARMING AND PREWARMING

RELATED APPLICATIONS

This application contains subject matter related to the subject matter of the following patent applications, all commonly owned herewith and all incorporated by reference:

Patent Cooperation Treaty (PCT) Application No. PCT/US2003/11128, filed Apr. 10, 2003, entitled "Patient Comfort Apparatus and System", and published on Oct. 23, 2003, under Publication No. WO 2003/086500;

PCT Application No. PCT/US2005/025355, filed Jul. 18, 2005, entitled "Perioperative Warming Device", and published on Feb. 23, 2006 under Publication No. WO 2006/020170;

PCT Application No. PCT/US2005/043968, filed Dec. 6, 2005, entitled "Warming Device with Varied Permeability", and published on Jun. 15, 2006 under Publication No. WO 2006/062910;

PCT Application No. PCT/US2005/044214, filed Dec. 6, 2005, entitled "Warming Device", and published on Jun. 15, 2006 under Publication No. WO 2006/063027;

PCT Application No. PCT/US2006/004644, filed Feb. 9, 2006, entitled "Warming Device for Perioperative Use", and published on Aug. 17, 2006 under Publication No. WO 2006/086587;

PCT Application No. PCT/US 2006/041028, filed Oct. 19, 2006, entitled "Multifunction Warming Device for Perioperative Use", and published on Apr. 26, 2007 under Publication No. WO 2007/047917;

PCT Application No. PCT/US2007/013073, filed Jun. 1, 2007, entitled "Warming Device", published on Jan. 31, 2008 under Publication No. WO 2008/013603;

PCT Application No. PCT/US2008/000141, filed Jan. 4, 2008, entitled "Convective Warming Device With a Drape";

U.S. patent application Ser. No. 10/411,411,431, filed Apr. 10, 2003, entitled "Forced Air Warming Unit" and published on Oct. 14, 2004 under Publication No. US 2004/0204748, now U.S. Pat. No. 6,876,884;

U.S. patent application Ser. No. 10/411,865, filed Apr. 10, 2003, entitled "Patient Comfort Apparatus and System" and published on Oct. 16, 2003 under Publication No. US 2003/0195596, now U.S. Pat. No. 7,001,416;

U.S. patent application Ser. No. 10/508,319, filed Sep. 20, 2004, entitled "Patient Comfort Apparatus and System" and published on Jun. 30, 2005 under Publication No. US 2005/0143796;

U.S. patent application Ser. No. 10/895,672, filed Jul. 21, 2004, entitled "Perioperative Warming Device", now abandoned, published on Jan. 20, 2005, under Publication No. US 2005/0015127;

U.S. patent application Ser. No. 11/005,883, filed Dec. 7, 2004, entitled "Warming Device with Varied Permeability" and published on Jun. 8, 2006 under Publication No. US 2006/0122671, now U.S. Pat. No. 7,226,454;

U.S. patent application Ser. No. 11/006,491, filed Dec. 7, 2004, entitled "Warming Device" and published on Jun. 8, 2006 under Publication No. US 2006/0122672;

U.S. patent application Ser. No. 11/057,396, filed Feb. 11, 2005, entitled "Perioperative Warming Device" and published on Aug. 17, 2006 under Publication No. US 2006/0184217, now U.S. Pat. No. 7,276,076;

U.S. patent application Ser. No. 11/057,397, filed Feb. 11, 2005, entitled "Thermal Blanket for Warming the Limbs" and published on Aug. 17, 2006 under Publication No. US 2006/0184216;

U.S. patent application Ser. No. 11/057,403, filed Feb. 11, 2005, entitled "Warming Device for Perioperative Use" and published on Aug. 17, 2006 under Publication No. US 2006/0184218;

U.S. patent application Ser. No. 11/260,706, filed Oct. 27, 2005, entitled "Patient Comfort Apparatus and System", and published on Mar. 9, 2006 under Publication No. US 2006/0052853;

U.S. patent application Ser. No. 11/363,136, filed Feb. 27, 2006, entitled "Forced Air Warming Unit" and published on Jul. 6, 2006 under Publication No. US 2006/0147320;

U.S. patent application Ser. No. 11/492,425, filed Jul. 25, 2006, entitled "Warming Device", and published on Nov. 16, 2006 under Publication No. US 2006/0259104;

U.S. patent application Ser. No. 11/583,432, filed Oct. 19, 2006, entitled "Multifunction Warming Device for Perioperative Use", and published on Apr. 26, 2007 under Publication No. US 2007/0093882;

U.S. patent application Ser. No. 11/583,477, filed Oct. 19, 2006, entitled "Multifunction Warming Device with Provision for Being Secured", and published on Apr. 26, 2007 under Publication No. US 2007/0093883;

U.S. patent application Ser. No. 11/583,480, filed Oct. 19, 2006, entitled "Multifunction Warming Device with Provision for Warming Hands", and published on Apr. 26, 2007 under Publication No. US 2007/0093884;

U.S. patent application Ser. No. 11/583,481, filed Oct. 19, 2006, entitled "Multifunction Warming Device with an Upper Body Convective Apparatus", and published on Apr. 26, 2007 under Publication No. US 2007/0093885;

U.S. patent application Ser. No. 11/656,777, filed Jan. 23, 2007, entitled "Convective Warming Device With a Drape";

U.S. patent application Ser. No. 11/704,547, filed Feb. 9, 2007, entitled "A Forced Air Warming Unit";

U.S. patent application Ser. No. 11/801,292, filed May 9, 2007, entitled "Warming Device with Varied Permeability", and published on Oct. 11, 2007 under Publication No. US 2007/023939;

U.S. patent application Ser. No. 11/899,872, filed Sep. 7, 2007, entitled "Perioperative Warming Method", and published on Jan. 31, 2008 under Publication No. US 2008/0027522; and, U.S. patent application Ser. No. 11/899,928, filed Sep. 7, 2007, entitled "Perioperative Warming Device" and published on Jan. 31, 2008 under Publication No. US 2008/0027521.

BACKGROUND OF THE INVENTION

A clinical garment has at least one duct in communication with permeable surfaces for delivery of warmed air by convection to the inside of the garment.

Convective devices that transfer heat to a human body are known. For example, there are devices that receive a stream of warmed pressurized air, inflate in response to the pressurized air, distribute it within a pneumatic structure, and emit the warmed air onto a body to accomplish such objectives as increasing comfort, reducing shivering, and treating or preventing hypothermia. These devices are typically called "convective thermal blankets" or "covers". Arizant Healthcare Inc., the assignee of this application, makes and sells such thermal blankets under the BAIR HUGGER® brand. One such device is the Model 522. Upper Body Blanket.

Use of the term "convective" to denote the transfer of heat between a warming device and a body refers to the principal mode of heat transfer, it being understood that heat may at the same time be transferred between a convective warming device and a body by conduction and radiation, although not to the degree of convection.

A recent invention disclosed in the referenced PCT application adapts a clinical garment such as a robe or gown to receive a convective warming device in order to warm a patient wearing the garment in a clinical setting for comfort and mobility of the patient. Arizant Healthcare Inc., the assignee of this application, makes and sells such warming devices under the BAIR PAWS® brand. There is a need to further adapt such a clinical garment in order to simplify the means by which it delivers warmed air and to enhance the utility of the garment in delivering perioperative thermal treatment to patients.

The term "perioperative" is defined in the *PDR Medical Dictionary*, Second Edition, (Medical Economics Company, 2000), as "around the time of operation." The perioperative period is characterized by a sequence including the time preceding an operation when a patient is being prepared for surgery ("the preoperative period"), followed by the time spent in surgery ("the intraoperative period"), and by the time following an operation when the patient is closely monitored for complications while recovering from the effects of anesthesia ("the postoperative period").

According to Mahoney et al. (Maintaining intraoperative normothermia: A meta-analysis of outcomes with costs. *AANA Journal*. 4/99;67,2:155-164.), therapeutic warming is employed during at least the intraoperative period (during surgery) in order to prevent or mitigate a constellation of effects that result from hypothermia. In fact, it is increasingly manifest that maintenance of normothermia perioperatively enhances the prospects for a quick, successful recovery from surgery. The effectiveness of therapeutic warming depends upon delivery of enough heat to a patient's body to raise the patient's core body temperature to, or maintain it within, a narrow range, typically near 37° C. This range is called "normothermic" and a body with a core temperature in this range is at "normothermia." Hypothermia occurs when the core body temperature falls below 36° C.; mild hypothermia occurs when core body temperature is in the range of 34° C. to 36° C. Therefore, "perioperative therapeutic warming" is warming therapy capable of being delivered during one or more of the perioperative periods for the prevention or treatment of hypothermia.

Therapeutic warming is contrasted with "comfort warming" which is intended to maintain or enhance a patient's sense of "thermal comfort". Of course, therapeutic warming may also comfort a patient by alleviating shivering or a feeling of being cold, but this is a secondary or ancillary effect. Thermal comfort is a subjective notion; however, the environmental conditions necessary to produce a sense of thermal comfort in a population of human beings are known and well tabulated. For example, Fanger (*Thermal Comfort: Analysis and Applications of Environmental Engineering*. Danish Technical press, Copenhagen, 1970) defines thermal comfort as "that condition of mind which expresses satisfaction with the thermal environment." Even when a patient is normothermic, less than ideal environmental conditions can result in acute feelings of discomfort. Under normothermic conditions, thermal comfort is largely determined with reference to skin temperature, not core body temperature. Comfort warming is warming applied to a patient to alleviate the patient's sense of thermal discomfort.

Both therapeutic warming and comfort warming may be provided by convective devices such as convective thermal blankets that receive and distribute warmed, pressurized air and then expel the distributed air through one or more surfaces toward a patient in order to prevent or treat hypothermia in the patient. An example of use of such a device for therapeutic warming is found in U.S. Pat. No. 6,524,332, "System and Method for Warming a Person to Prevent or Treat Hypothermia", commonly owned with this application. Comfort warming by a clinical garment is described in the referenced U.S. Patent Application, and the referenced Publication No. WO 03/086500.

When delivered by convective devices, therapeutic warming is distinguished from comfort warming by intended effects and by the parameters of heat delivery that produce those effects. In this regard, a convective warming system typically includes a source of warmed pressurized air (also called a heater/blower unit, a forced air warming unit, a heater unit, etc.), a convective device such as a thermal blanket (which is, typically, inflatable), and a flexible conduit or air hose connecting the heater/blower unit with the thermal blanket. Use of such a system for a particular type of warming requires delivery of warmed air through a thermal blanket at parametric values that achieve a particular objective. The conditions by which a convective device such as a thermal blanket produces thermal comfort in normothermic individuals at steady state are significantly different from those necessary to treat hypothermia. Typically the conditions for thermal comfort are met in a comfort warming system with a relatively low capacity heater/blower unit, while those in a therapeutic warming system are achieved with a relatively high capacity heater/blower unit. The different capacities have led to use of air hoses with different capacities, with those delivering air flow for thermal comfort typically having smaller diameters than those serving a therapeutic warming requirement. The result is a divergence of designs leading to installation of different air delivery infrastructures for therapeutic and comfort warming.

The application of warmed air to the limbs by a comfort warming system produces the sense of well-being that characterizes comfort warming because of the high density of thermoreceptors in the arms and legs. Warming the peripheral body regions produces a greater comfort response than thermal stimulation of the anterior or posterior abdominal and thoracic body regions. One surprising result of warming preoperatively by heating the limbs is that the increase of thermal energy content in the body's periphery prevents or reduces the core temperature drop caused by core-to-periphery redistribution. Thus, while warming the limbs preoperatively does not produce an increase in core body temperature, it does prevent that temperature from dropping once anesthesia is initiated. Warming the limbs preoperatively in order to prevent or delay a drop in core body temperature may be referred to as "prewarming."

The comfort warming system described in the referenced Publication No. WO 03/086500 directs warmed air primarily to the thoracic and upper abdominal regions. Its utility for prewarming is therefore limited. Adaptation of a clinical garment for both comfort warming and prewarming would enhance the utility of such comfort warming systems and provide greater flexibility in thermal treatment of patients.

SUMMARY

In one aspect, a clinical garment has at least one duct in communication with permeable surfaces along peripheral portions of the inside of the garment.

In another aspect, the permeable surfaces are disposed along a lower hem portion and along lower sleeve portions on the inside of the garment.

In yet another aspect, the duct may be formed integrally with the clinical garment.

BRIEF DESCRIPTION OF THE DRAWINGS

FIGS. 3A-3F are views showing assembly of the clinical garment for comfort warming and prewarming, in which FIG. 3A is a plan view of a major garment piece, FIG. 3B is a plan view of two sleeve pieces, FIG. 3C is a plan view of the major garment piece after folding, FIG. 3D is a plan view of the two sleeve pieces after folding, FIG. 3E is a plan view of the folded pieces after a first assembly step, and FIG. 3F is a front elevation view of the clinical garment fully assembled.

SPECIFICATION

A warming device is constituted of a clinical garment with at least one duct for comfort warming and prewarming. In this regard, a "clinical garment" is a garment that is typically used to temporarily clothe a patient in a clinical setting. Clinical garments include hospital gowns, robes, bibs and other equivalents. The clinical setting may be a medical or dental office or clinic, a hospital, or any facility or institution that provides medical or dental treatment to patients. The clinical garment has a duct in communication with permeable surfaces on the inside of the clinical garment for comfort warming and prewarming by convection. The permeable surfaces are disposed along peripheral portions of the inside of the garment. For example, the permeable surfaces may be disposed along a lower hem portion and along lower sleeve portions on the inside of the garment. When a patient wears the clinical garment, the patient's legs extend across the permeable surface along the lower hem portion while the patient's arms extend along the permeable surfaces along the lower sleeve portions. Delivery of warmed pressurized air through these surfaces to the patient's limbs provides comfort warming and also prewarming.

In one aspect, a clinical garment with a duct for comfort warming and prewarming may be worn on a patient where it receives a stream of warmed pressurized air in through an inlet port of the duct and emits the air through one or more permeable surfaces near peripheral potions of the inside of the clinical garment to convectively warm the patient's limbs for comfort and for prewarming.

In another aspect, a clinical garment for prewarming may be worn on a patient while of warmed pressurized air is received in the duct and distributed by the duct to one or more permeable surfaces on the inside of the clinical garment near the patient's limbs.

In the clinical garment illustrated and discussed below, the duct is inflatable. That is, the structure of the duct, flaccid when not in use, tautens when receiving a stream of pressurized air.

Figure 1:
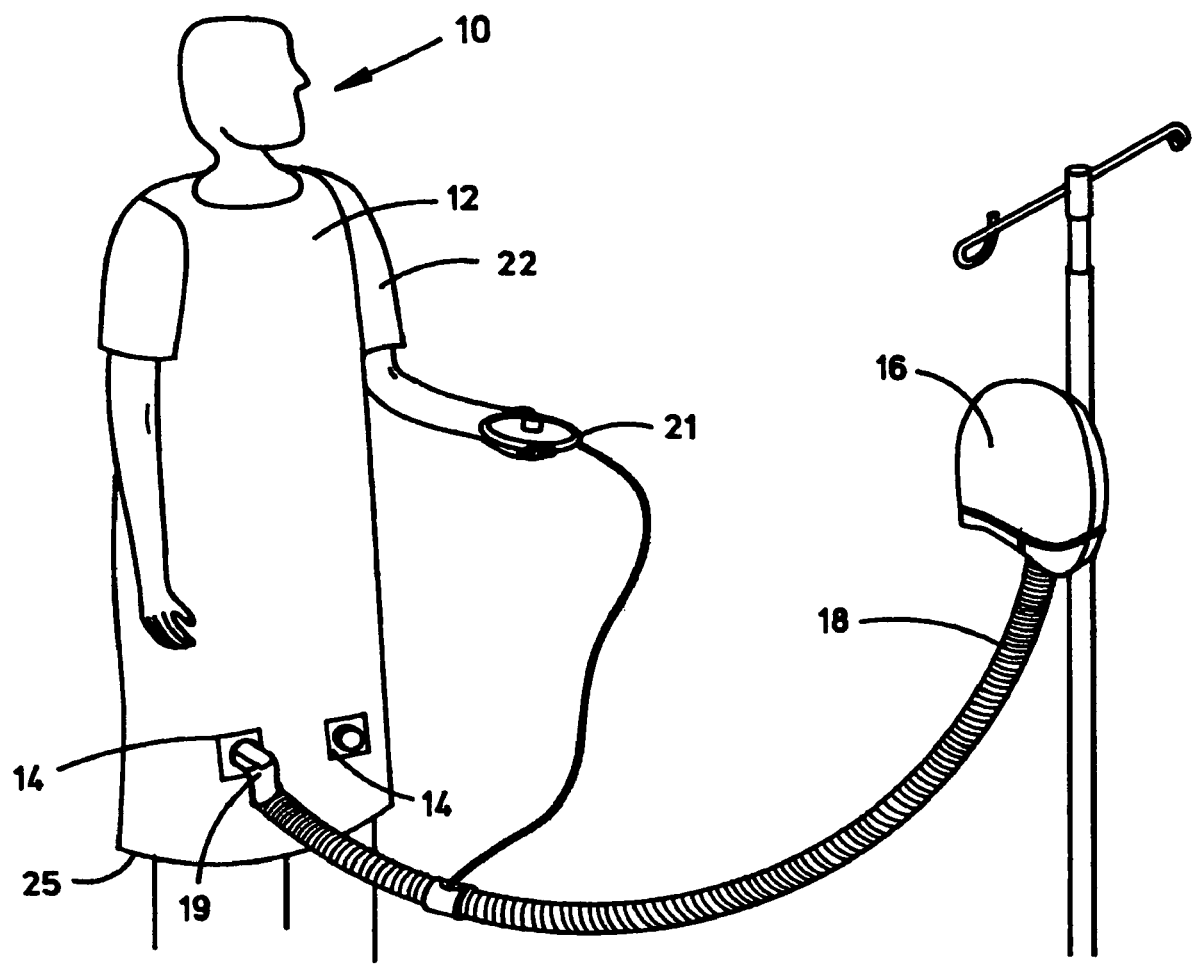
FIG. 1 is an illustration of a patient wearing a clinical garment for comfort warming and prewarming.

Refer now to FIG. 1 in which a patient 10 wearing a clinical garment 12 for comfort warming and prewarming is shown. The patient is shown standing although the patient may also sit or recline while wearing and being warmed by the clinical garment 12. The clinical garment 12 includes at least one duct which communicates warmed pressurized air to permeable surfaces on the inside of the clinical garment 12. The permeable surfaces are disposed near peripheral portions of the clinical garment 12 where the patient's limbs are disposed when the patient wears the clinical garment 12.

At least one inlet port 14 including a collar of material mounted to an outside of the clinical garment and an opening through the collar into the duct is provided through which the duct may receive warmed pressurized air from a heater/blower unit 16. An air hose 18 with a nozzle 19 conducts a stream of warmed pressurized air to the duct. In FIG. 1, the nozzle 19 is received in an inlet port 14. The patient is enabled to control at least the temperature of the warmed air by way of controller 21. The warmed air source 18, 19, 21 is illustrative and not intended to limit the principles being described. Another representative forced air warming unit which may be used to provide a stream of warmed pressurized air is specified in detail in referenced U.S. patent application Ser. No. 10/411,431, now U.S. Pat. No. 6,876,884.

Most convective warming products are designed to provide a single mode of warming. Each of the thermal blankets described above is designed for therapeutic warming. The devices described in publication WO 03/086500 are designed for comfort warming. In contrast, the clinical garment described in this specification may provide either comfort warming and/or prewarming, depending on the need.

Figure 2:
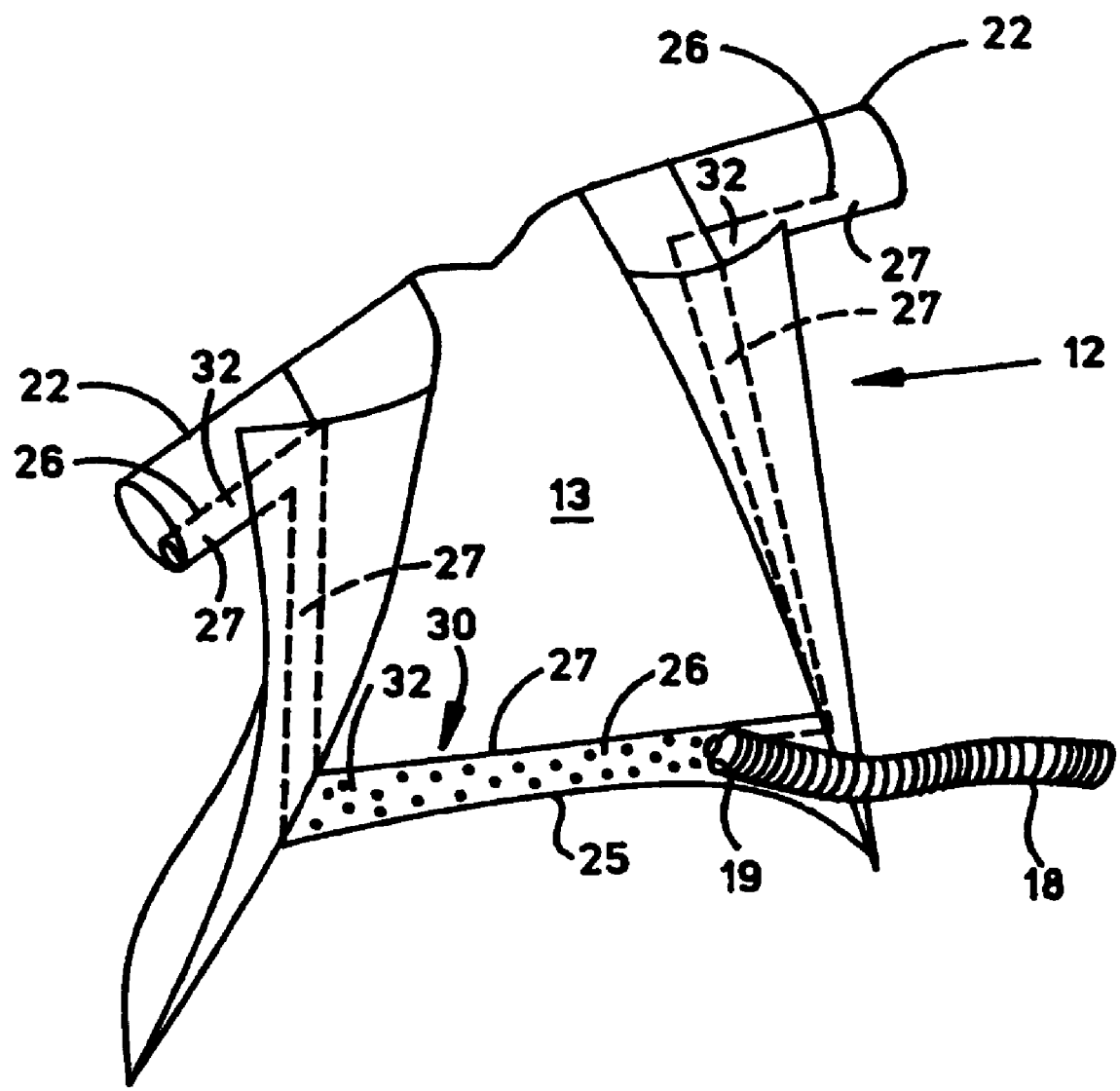
FIG. 2 illustrates a view toward the inside of the clinical garment showing permeable surfaces and a duct.

The clinical garment 12 for comfort warming and prewarming is illustrated in FIGS. 1 and 2. The clinical garment 12 is seen from one side (the back, for example) in FIG. 2, looking at its inside surface 13. As seen in FIGS. 1 and 2, the clinical garment 12 has two sleeves 22 and a lower hem 25. Inside the clinical garment 12 there are one or more permeable surfaces, one indicated by 26. In this regard a permeable surface is a surface of a permeable member, such as a portion of a tube or tubular duct. The portion is permeable in that warmed pressurized air can circulate from inside the tubular duct through the portion and its permeable surface. The portion is permeable either from having apertures formed in it or from being made of a material having a permeable structure. The permeable portion may be a portion of the duct that faces toward the inside of the clinical garment 12. The duct is indicated by reference numeral 27. As seen in FIG. 2, the duct 27 extends along the lower hem 25, rises to the sleeves 22, and extends inside the sleeves 22, along lower portions thereof. The permeable surfaces 26 may include the surface portion 30 of the duct 27 inside the clinical garment 12 along the lower hem 25. The permeable surfaces 26 may further include the surface portions 32 of the duct 27 inside the lower portions of the sleeves 22. Circulation of warmed pressurized air from within the duct 27 through a permeable surface 26 is indicated by arrows 32. As seen in FIG. 1, the positioning of the permeable surfaces 26 along the lower hem 25 and the lower portions of the sleeves 22 disposes those permeable surfaces 26 adjacent the legs and arms of the patient 10 for warming the legs and arms by convection.

Figure 3A:
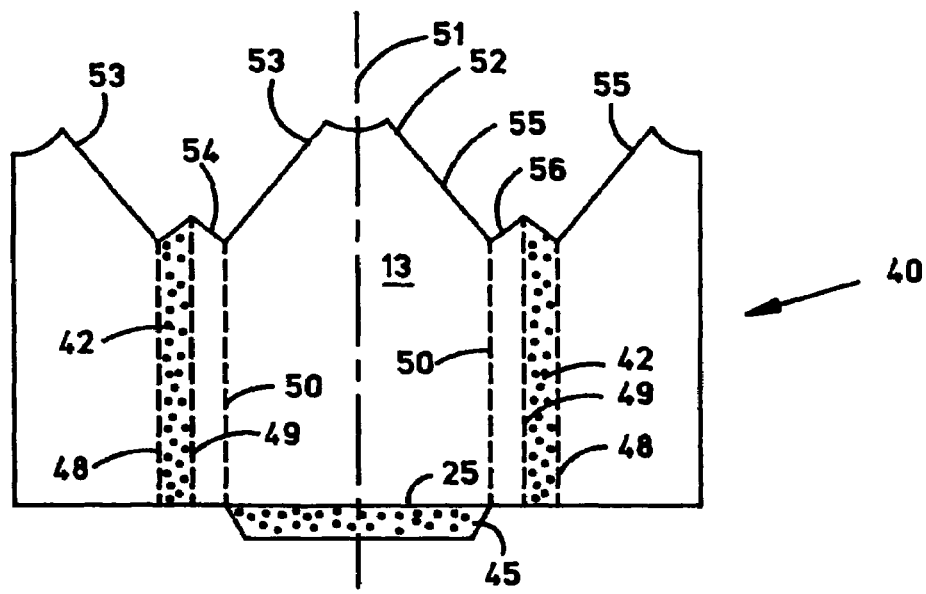
Figure 3B:
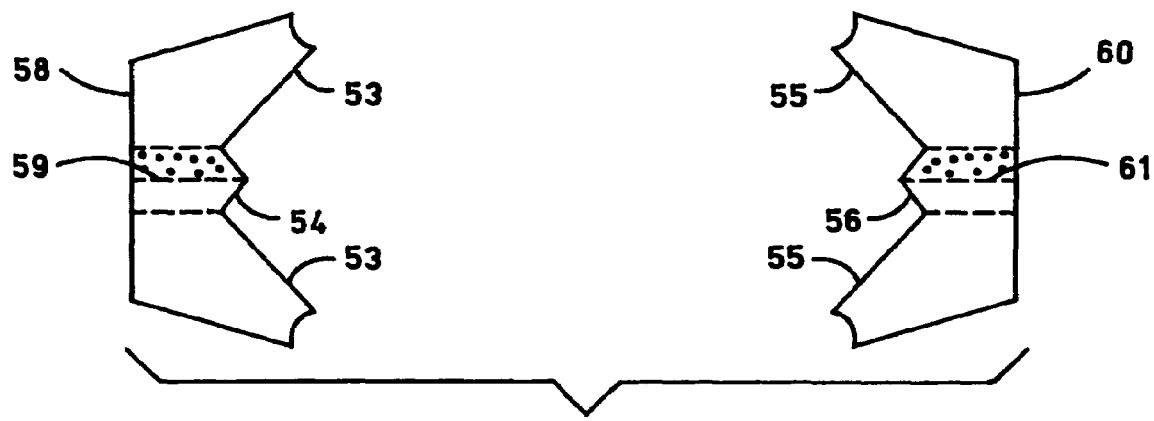
Figure 3C:
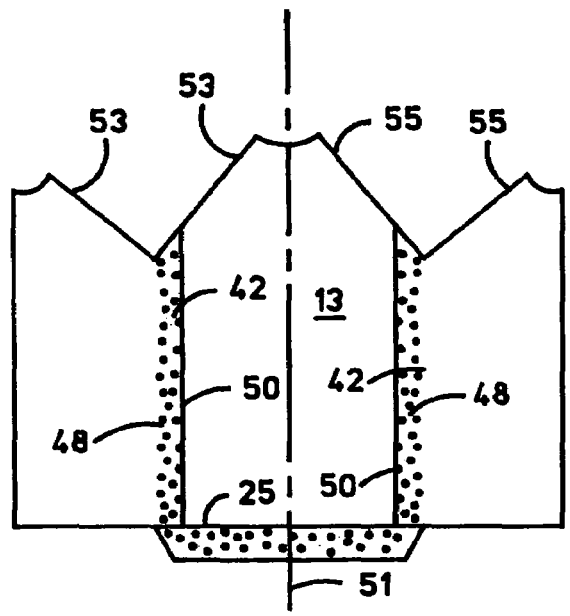
Figure 3D:
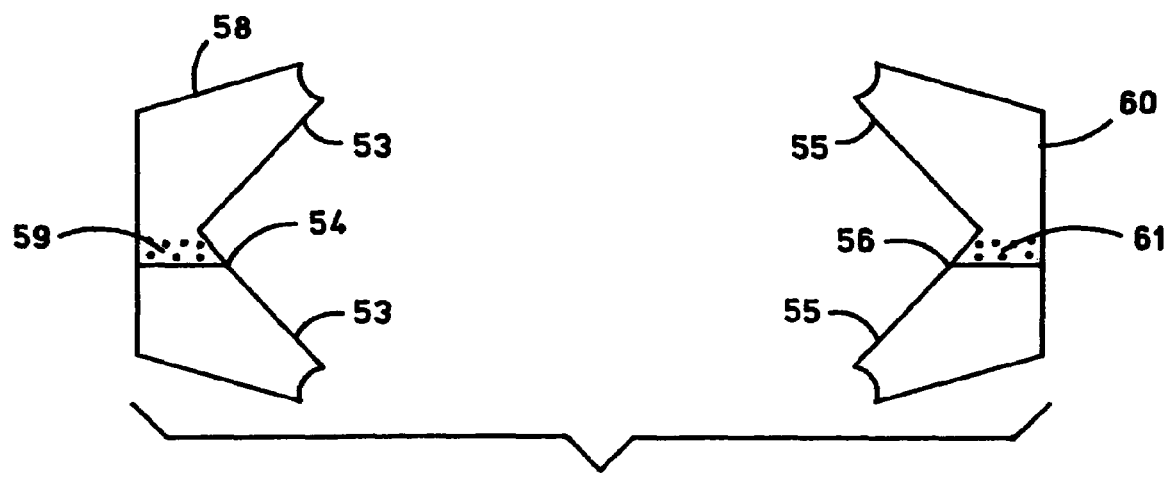
Figure 3E:
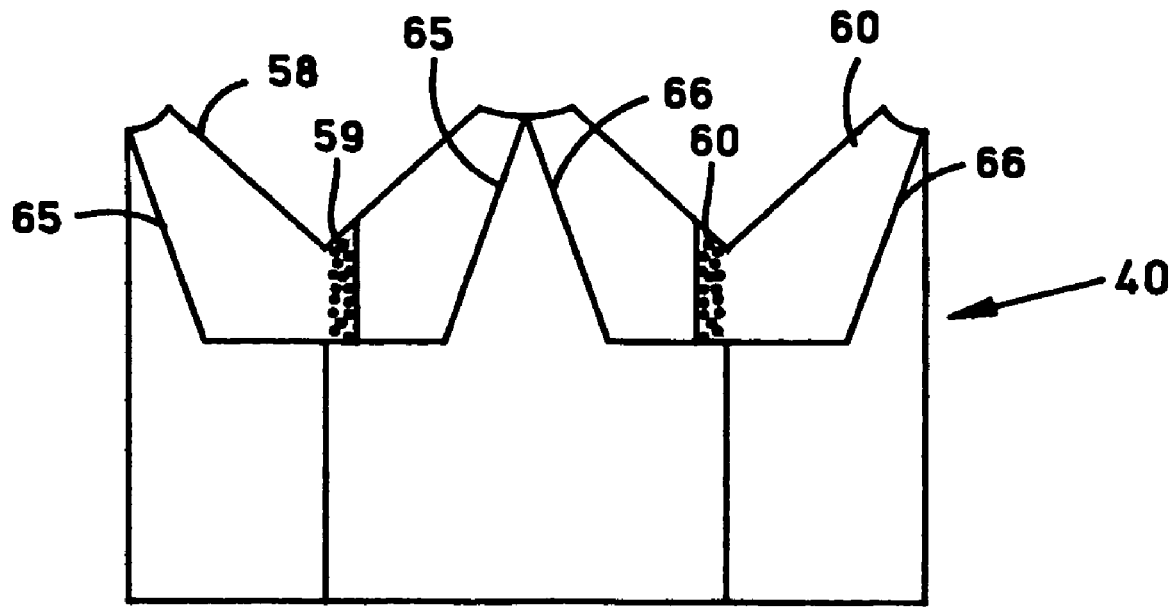
Figure 3F:
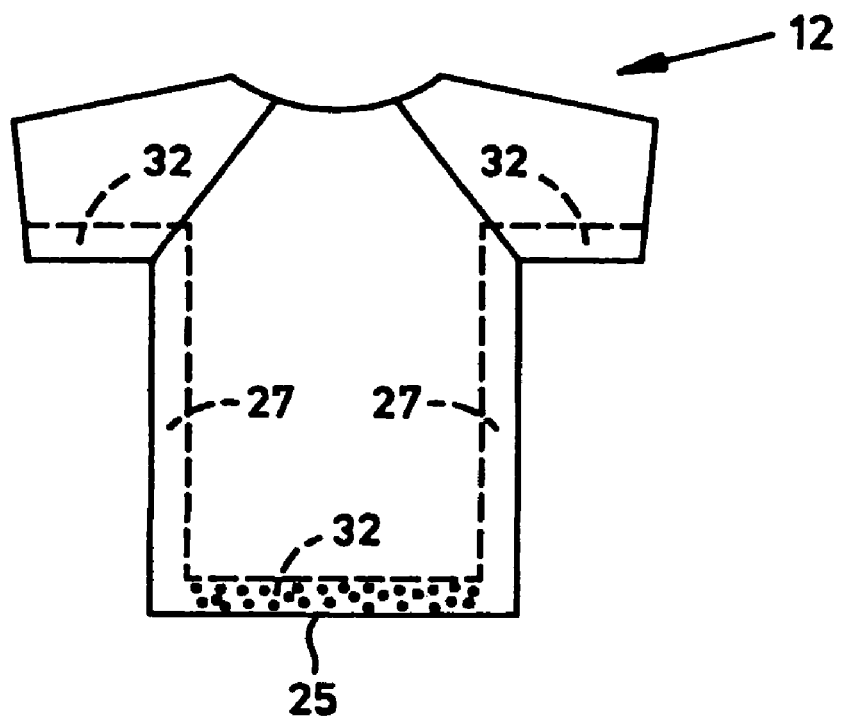

With reference to FIGS. 2 and 3A-3F, a representative assembly of the clinical garment 12 will be specified. FIG. 3A shows a first piece 40 of material constituting a major garment piece. The first piece 40 is viewed in plan, with the inside surface 13 of the clinical garment visible, although this orientation is selected only to aid this description. The first piece 40 is relatively impermeable with permeable duct portions 42 and a permeable lower hem portion 45. The duct and hem portions 42 and 45 may be integral parts of the piece 40 that have had apertures formed therein to render them permeable. Alternatively, the first piece 40 may be made of permeable material treated to leave all but the portions 42 and 45 impermeable. Parallel folding lines 48 and 49 are defined on respective borders of the duct portions 42, and a respective folding line 50 is defined between each folding line 49 and a center midline 51 of the clinical garment. The upper edge 52 of the first piece 40 includes sleeve edges 53 and point 54 on the left side of the upper edge 52 and sleeve edges 55 and point 56 on the right side of the upper edge 52. In FIG. 3B, two sleeve pieces 58 and 60 are shown. Each has a respective elongate permeable section 59 and 61. An inner edge of the sleeve piece 58 has sleeve edges 53 and point 54 that correspond to the identically-numbered features on the first piece 40 and an inner edge of the sleeve piece 60 has sleeve edges 55 and point 56 that correspond to the identically-numbered features on the first piece 40. As shown in FIGS. 3C and 3D, permeable ducts are formed on either side of the midline 51. In this regard, the first piece is double-Z folded toward the midline 51 along parallel folding lines 48, 49, and 50, and the edges at the folding lines are secured (by sealing, gluing, or sewing, for example) to the inside surface 13. The ducts are indicated by the duct portions 42. The hem portion 45 is folded upwardly toward the inside surface 13 along the lower hem line 25 and the upper edge of the hem portion is secured by a seal to the inside surface 13 and over the side ducts 42 where overlap occurs. The sleeve pieces are double-Z folded and sealed along the elongate edges of the permeable sections 59 and 61. As shown in FIG. 3E, the folded sleeve pieces are matched to and attached (by sealing, gluing, or sewing, for example) to the folded first piece along the upper edge 52. The edges 65/65 and 66/66 are secured together (by sealing, gluing, or sewing, for example) to form the sleeves 22. The result, shown in FIG. 3F, is the clinical garment 12 with the elements illustrated in FIG. 2 and described above.

Manifestly, the descriptions and illustrations in this specification are presented for an understanding of how to make and use an exemplary perioperative warming device. The only limitations on the scope of protection afforded the inventive principles presented are in the following claims.

The invention claimed is:

1. A device to warm a person's limbs, comprising:
   a clinical garment with a lower hem, an inside and sleeves;
   at least one permeable surface on the inside of the clinical garment near a peripheral portion of the clinical garment;
   a single tubular duct on the clinical garment in communication with the at least one permeable surface, the duct extending along the lower hem, rising along the inside to the sleeves, and extending inside the sleeves; and
   at least one inlet port opening into the duct.

2. The device of claim 1 in which the duct is formed integrally with the garment.

3. The device of claim 1 in which the peripheral portion includes the lower hem.

4. The device of claim 1 in which the peripheral portion includes an elongate lower portion of each sleeve.

5. The device of claim 4 in which the peripheral portion further includes the lower hem.

6. The device of claim 5 in which the duct is formed integrally with the clinical garment.

7. The device of claim 6 in which the clinical garment includes at least two pieces of material joined along corresponding peripheries, a first piece of material having peripheral permeable sections overlapping a second piece of material, wherein the duct is formed by spaced-apart seams joining an inward fold of the peripheral permeable sections to the second piece.

8. The device of claim 7 in which the material is a woven or a non-woven material.

9. The device of claim 7 in which the at least one inlet port includes a collar of material mounted to an outside of the clinical garment and an opening through the collar into the duct.

10. A clinical garment for warming a person, comprising:
    a lower hem, an inside surface, and sleeves;
    a single tubular duct on the inside surface, extending along the lower hem;
    the duct including a permeable portion along the lower hem; and
    at least one inlet port opening into the duct.

11. A clinical garment for warming a person, comprising:
    a lower hem, an inside surface, and sleeves;
    a single tubular duct extending along the lower hem, rising along the inside of the clinical garment to the sleeves, and extending along lower inside portions of the sleeves;
    the duct including a permeable portion along the lower inside portion of each sleeve; and
    at least one inlet port opening into the duct.

12. A clinical garment for warming a person, comprising:
    the clinical garment with a lower hem, an inside and sleeves;
    a permeable surface on the inside of the clinical garment near a lower hem of the clinical garment;
    two permeable surfaces on the inside of the clinical garment, each near a lower portion of a sleeve of the clinical garment;
    a single tubular duct in communication with all the permeable surfaces, the duct having portions extending along the lower hem and inside the lower portions of the sleeves; and
    at least one inlet port opening into the duct.

13. The clinical garment of claim 12 in which the clinical garment includes at least two pieces of material joined along corresponding peripheries, a first piece of material having peripheral permeable sections overlapping a second piece of material, wherein the duct is formed by spaced-apart seams joining an inward fold of the peripheral permeable sections to the second piece.

14. The clinical garment of claim 13 in which the material is a woven material.

15. The clinical garment of claim 13 in which the material is a non-woven material.

16. The clinical garment of claim 13 in which the at least one inlet port includes a collar of material mounted to an outside of the clinical garment and an opening through the collar into the duct.

17. A method for warming a person using a warming device constituted of a clinical garment with a lower hem, an inside, and sleeves, permeable surfaces on the inside of the clinical garment along the lower hem and lower inside portions of the sleeves, and a single tubular duct in communication with the permeable surfaces, the method comprising:
    dressing a person with the clinical garment such that the permeable surfaces are disposed adjacent portions of the limbs of the person;
    coupling the duct to a source of warmed pressurized air; and
    warming the person by convection directed only at the limbs by way of the permeable surfaces.

* * * * *

UNITED STATES PATENT AND TRADEMARK OFFICE
CERTIFICATE OF CORRECTION

PATENT NO. : 7,470,280 B2
APPLICATION NO. : 11/057404
DATED : December 30, 2008
INVENTOR(S) : Mark T. Bieberich It is certified that error appears in the above-identified patent and that said Letters Patent is hereby corrected as shown below:

Title Page, Item [56]
Under the heading U.S. PATENT DOCUMENTS
    column 2, line 3 replace "4,696,066 A 9/1987 Ball et al." with "4,696,066 A 9/1987 Ball et al. 2/272".

Title Page, Page 2
Under the heading U.S. PATENT DOCUMENTS
    column 1, line 24, replace "6,551,347 B1 4/2003 Elkins" with "6,551,347 B1 4/2003 Elkins 607/104".
    column 1, line 36, replace "7,364,584 B2 4/2008 Anderson" with "7,364,584 B2 4/2008 Anderson 607/108".
    column 2, line 5, replace "2008/0027521 A1 1/2008 Bieberich" with "2008/0027521 A1 1/2008 Bieberich 607/96".
    column 2, line 6, replace "2008/0027522 A1 1/2008 Bieberich" with "2008/0027522 A1 1/2008 Bieberich 607/96".

Column 1, line 37
Delete "Ser. No. 10/411,411,431" and replace it with "Ser. No. 10/411,431".

Column 2, line 64
Delete "." after the number "522".

Column 5, line 48 to 49
Delete the paragraph separation between line 48 ending with "for prewarming." and line 49 beginning with "In another aspect,".

Column 5, line 50
Add "a stream" after the word "while".

Column 5, line 53
After "limbs." add "The warmed pressurized air may circulate through the permeable surfaces to warm the patient's limbs.".

Signed and Sealed this

Fifth Day of January, 2010

David J. Kappos
*Director of the United States Patent and Trademark Office*